United States Patent [19]

Mizuno et al.

[11] 4,350,679
[45] Sep. 21, 1982

[54] SOFT CAPSULE COATED WITH A FILM OF CARNAUBA WAX AND PROCESS FOR THE PREPARATION OF THE SAME

[75] Inventors: Yasuhiko Mizuno, Kagamihara; Masanori Kayano, Honjo, both of Japan

[73] Assignee: Eisai Co., Ltd., Tokyo, Japan

[21] Appl. No.: 253,626

[22] Filed: Apr. 13, 1981

[30] Foreign Application Priority Data

May 8, 1980 [JP] Japan .................................. 55-59981

[51] Int. Cl.$^3$ .......................... A61K 9/42; A61K 9/48
[52] U.S. Cl. ........................................ 424/38; 424/37; 427/3
[58] Field of Search ..................... 424/37, 38; 427/2, 3

[56] References Cited

U.S. PATENT DOCUMENTS

| | | | |
|---|---|---|---|
| 2,491,475 | 12/1949 | Bogin | 424/37 |
| 3,197,369 | 7/1965 | Widmann et al. | 424/37 |
| 3,438,797 | 4/1969 | Biddle | 424/38 |
| 3,456,051 | 7/1969 | Mima et al. | 424/37 |
| 3,467,748 | 9/1969 | Widmann | 424/37 |
| 3,576,665 | 4/1971 | Chelken et al. | 424/38 |
| 3,592,945 | 7/1971 | Engelking | 424/37 |
| 4,138,013 | 2/1979 | Okajima | 424/37 |

FOREIGN PATENT DOCUMENTS

461317  2/1937  United Kingdom .................. 424/38

*Primary Examiner*—Shep K. Rose
*Attorney, Agent, or Firm*—Blanchard, Flynn, Thiel, Boutell & Tanis

[57] ABSTRACT

A soft-gelatin capsule having a coating film layer of carnauba wax on the outer surface of the soft-gelatin shell. Preferably, the amount of the carnauba wax is at least 0.002 part by weight based on 100 parts by weight of the amount of the soft-gelatin shell.

4 Claims, No Drawings

SOFT CAPSULE COATED WITH A FILM OF CARNAUBA WAX AND PROCESS FOR THE PREPARATION OF THE SAME

This invention relates to a soft capsule comprising pharmaceutically active contents and a coated shell.

The soft capsule dosage form is conveniently employed for encapsulating an oily liquid, granules, a pellet or the like. Particularly, the rotary process is at present extensively applied to the preparation of soft capsules. However, it has been pointed out that the soft capsule has inherent drawbacks described below.

The sheel of the soft capsule generally comprises gelatin, glycerol and water as the main components. Accordingly, the soft capsule can be kept in a satisfactory condition as long as the water content of the shell is maintained within a certain range. It is empirically known that the water content is preferably maintained in the range of 5–10% for the shell of a soft capsule. However, the water content of the soft capsule is apt to vary depending upon deviations in the ambient conditions from the above-mentioned preferred range in the course of time. If the water content reaches so high a level as to exceed the upper limit of the preferred range, the shell becomes wet and softens. The soft capsule under these conditions shows poor lubricity and glidability so that the operations for packing the capsules cannot be carried out smoothly. Moreover, the soft capsules are apt to stick to each other to form an aggregated mass. On the other hand, if the water content reaches a low level below the above-mentioned lower limit, the shell hardens to produce cracks therein.

For these reasons, a measure for maintaining the water content of the shell within the above-mentioned preferred range has been a subject to be studied. Nevertheless, there has not been developed an appropriate measure for solving this problem in the art. At present, there is generally employed a treatment process which comprises treating a soft capsule with liquid paraffin and/or chlorothene immediately after the preparation of the capsule. This treatment process, however, is done to keep the capsules separate from each other and also to wash the surface of the capsule. Accordingly, this treatment is hardly effective for maintaining the water content of the shell of the soft capsule at a certain level.

In view of these problems, the present inventors have made a variety of studies for developing a measure for maintaining the water content of the shell of the soft capsule. As a result, they have found that treatment of the surface of the soft capsule with carnauba wax is effective to accomplish the desired object. This invention has been completed based on this finding.

According to the studies of the inventors, only carnauba wax effectively inhibits the change of the water content of the shell of the soft capsule which is apt to take place with the passage of time.

The soft capsule of the invention comprises pharmaceutically active contents and a shell that is composed of gelatin (main component) and a water-preserving agent such as glycerol or sorbitol, and is adjusted to have a water content of approximately 5–10%. The pharmaceutically active contents enclosed inside of the shell may be an oily liquid, granules, a pellet or the like, containing pharmaceuticals. Examples of the soft capsule of the invention include a soft gelatin capsule which is charged with an oily liquid containing Vitamin E.

There is no limitation on the form of the carnauba wax to be employed for the invention. In order to facilitate the procedure of the surface coating, however, the carnauba wax preferably is in the form of a powder such as powdery carnauba wax available from Toa Kasei Co., Ltd., Japan.

Carnauba wax is at present employed as a base material of an ointment, a glazing agent for pellets, a hardening agent of a cosmetic stick, etc. The use of it for the surface coating of a soft capsule of the invention is not known, as far as the present inventors are aware.

The procedure for the surface coating according to the invention can be practically carried out, for instance, in the following manner.

The above-mentioned powdery carnauba wax is, in the first place, screened on a sieve of 80 meshes to make the particle sizes uniform. The so pre-treated carnauba wax is then sprinkled over the soft capsules tumbling in a coating pan. There is, however, no limitation on the coating procedure, so far as the carnauba wax can be coated uniformly over the surfaces of the soft capsules. Accordingly, the coating procedure disclosed herein is not given to restrict the invention.

As an embodiment of the process, it is preferred that powdery carnauba wax and soft capsules are introduced in a pan and the coating is conducted while rotating the pan and blowing warm air into the pan. The warm air is intermittently blown so that the carnauba wax may be kept molten and thereby adhere to the capsule effectively.

The amount of carnauba wax required for coating the surface of the soft capsules varies depending upon the water content of the shell. According to the experimental results, carnauba wax is required in the amount of at least 0.002 part by weight per 100 parts by weight of the amount of the shell, if the water content of the shell is to be kept at 5%. In other examples, if the water content is to be kept at 8% or 10%, carnauba wax is required in the amount of at least 0.004 to 0.006 part by weight, respectively.

There is no specific reason to set the upper limit of the amount of carnauba wax to be coated. In view of the value as a product supplied commercially, the amount of carnauba wax is preferably set at 0.15 part by weight on the same basis. If carnauba wax is employed in such an increased amount, the water content is effectively preserved at a higher level during the storage, as seen from the hereinafter-given data showing the effect of the invention. Further, the glidability of the soft capsules so coated becomes improved enhancing the operational efficiency of the packing stage. Furthermore, the soft capsule comprising the coating film layer of carnauba wax of the invention shows no remarkable retardation of disintegration in the disintegration test stipulated in the Japanese Pharmacopoeia, as seen from the experimental results given hereinafter, even though it is expected that the surface coating with wax generally causes an increase of the water repulsion and retards the disintegration of the capsule. Accordingly, there is no specific reason to set the upper limit of the amount of carnauba wax to be coated on the soft capsule. However, an increased amount of carnauba wax is apt to give a cloudy coating layer over a transparent soft capsule, so that the capsule cannot keep its transparency. This causes some problem in evaluating the capsule as a commercial product. In order to prevent the transparent soft capsule from being tinted with noticeable cloudiness, the amount of carnauba wax employed for the coating is preferably set to an amount of not higher than 0.05 part by weight. However, this is not the case for an opaque soft capsule containing titanium oxide in the shell.

For these opaque soft capsules, the preservability and glidability only should be taken into consideration, and accordingly an amount more than 0.05 part by weight can be coated thereon. Although an example showing the use of the maximum value of 0.15 part by weight of carnauba wax is provided hereinafter in the description on the examples showing effects of the invention, the value is not presented to restrict the amount of the coating of carnauba wax.

Replacement of a portion of the carnauba wax with other wax such as beeswax, haze wax or Japan wax (a kind of wood wax), triglyceride, and so forth does not present any remarkable advantage to the soft capsule, in comparison with the simple use of carnauba wax. However, the use of such replacement waxes should be considered to be included in the scope of the invention.

Whether the constitution of the soft capsule of the invention is realized on the soft capsule in question can be generally ascertained through observing an improved preservability. For more reliable confirmation, an appropriate analysis can be applied to the capsule.

The effects of the invention are illustrated by the following examples.

EXAMPLE ON EFFECTS 1

Sample: Soft capsules coated with carnauba wax of eight different amounts, in which the amounts are indicated by relative values to the amount of the shell originally provided to the soft capsule. The soft capsules were prepared in the manner as set forth in the hereinafter-given Preparation Example 1 to have a water content (of the shell) of 8%.

Procedure: In a glass bottle were placed 100 capsules, and the capsules were allowed to stand for six months under four different conditions (temperature and relative humidity) set forth in Table 1. The results were judged according to the following classification to indicate the four ranges from A to D.

A ... All of the 100 capsules fall instantly from the glass bottle when the bottle is placed upside down.

B ... One to five capsules stick and fail to fall from the glass bottle when the bottle is placed upside down. The so sticking capsules fall when the bottle is given a light shock.

C ... Six to ten capsules stick and fail to fall from the glass bottle when the bottle is placed upside down. The so sticking capsules fall when the bottle is given a hard shock.

D ... Ten to thirty pieces of the capsules stick and fail to fall from the glass bottle when the bottle is placed upside down. The so sticking capsules fall when the bottle is given a hard shock.

Results: Set forth in Table 1.

TABLE 1

| Amount of coating (%) | Conditions for Preservation | | | |
| --- | --- | --- | --- | --- |
|  | 4° C. 40% | 25° C. 42% | 37° C. 45% | 37° C. 75% |
| 0 | A | B | C | D |
| 0.002 | A | A | B | C |
| 0.004 | A | A | A | B |
| 0.006 | A | A | A | A |
| 0.01 | A | A | A | A |
| 0.05 | A | A | A | A |
| 0.10 | A | A | A | A |

TABLE 1-continued

| Amount of coating (%) | Conditions for Preservation | | | |
| --- | --- | --- | --- | --- |
|  | 4° C. 40% | 25° C. 42% | 37° C. 45% | 37° C. 75% |
| 0.15 | A | A | A | A |

As seen from Table 1, the soft capsules according to the invention stick neither to the inner surface of the glass bottle, nor to each other.

In Table 1, the amount of the coating of 0.002% means that the coating was done in the amount of 0.002 part by weight of carnauba wax based on 100 parts of the amount of the shell of the untreated soft capsule. This manner for indication of the amount of the coating will be applied in the same way in the following examples.

EXAMPLE OF EFFECTS 2

Sample: The same capsules as described in the previous Example on Effects 1 were used.

Procedure: The samples were immersed in a first test fluid prepared according to the description of the disintegration test stipulated in the Japanese Pharmacopoeia, 9th revision. The test solution was maintained at 37° C., and the period of time required for the initiation of disintegration of the capsule sample and release of the contents to the solution was determined to indicate the disintegration period.

The glidability of the capsule was tested on the operational efficiency in the stage for packing the capsules with PTP package material, that is, the gliding property of the capsule was observed in the PTP packing stage to evaluate the glidability, either poor or good.

The transparency of the capsule was evaluated according to the following judgement standard to classify the capsules into four grades from a to d.

a ... transparent
b ... slightly cloudy
c ... cloudy
d ... very cloudy

Results: Set forth in Table 2.

TABLE 2

| Amount of coating (%) | Evaluation Subjects | | |
| --- | --- | --- | --- |
|  | Disintegration Period (min.) | Glidability | Transparency |
| 0 | 6–8 | Poor | a |
| 0.002 | 6–8 | Poor | a |
| 0.004 | 6–8 | Good | a |
| 0.006 | 6–8 | Good | a |
| 0.01 | 6–8 | Good | b |
| 0.05 | 6–8 | Good | b |
| 0.10 | 7–10 | Good | c |
| 0.15 | 7–10 | Good | d |

As seen from Table 2, the increase of the amount of carnauba wax does not influence the disintegration period, beyond the increase within the range indicated in Table 2. The glidability increases as the amount of carnauba wax is increased. However, the transparency of the capsule drastically diminishes when the amount of the coating of carnauba wax exceeds 0.05%.

EXAMPLE OF EFFECTS 3

Sample: The same capsules as described in the previous Example on Effects 1 were used, except that the water content of the shell was set at 5% or 10%.

Procedure: The capsules were stored at 37° C. for six months. The results were judged according to the classification described in Example on Effects 1 and indicated by the same symbols.

Results: See Table 3. In Table 3, the data includes the data obtained on the soft capsule whose shell had the water content of 8% under conditions of the temperature of 37° C. and the relative humidity of 45%, which was previously incorporated in Table 1.

The data incorporated in Table 3 teaches that the minimum amounts of the carnauba wax coating film layer are 0.002%, 0.004% and 0.006% (as defined before, the relative percentage to the amount of the shell of the soft capsule) for capsules with shells having water contents of 5%, 8%, and 10%, respectively.

TABLE 3

| Amount of coating (%) | Water Content of Shell | | |
|---|---|---|---|
| | 5% | 8% | 10% |
| 0 | B | C | D |
| 0.002 | A | B | C |
| 0.004 | A | A | B |
| 0.006 | A | A | A |
| 0.01 | A | A | A |
| 0.05 | A | A | A |
| 0.10 | A | A | A |
| 0.15 | A | A | A |

The process for the preparation of the soft capsules is further illustrated by the following examples.

PREPARATION EXAMPLE 1

Three thousand Oval-3 type soft capsules, each of which contained 100 mg. of acetate of Vitamin E and the total weight of the shells of which was 285 g. were charged and tumbled in a pan of an inner diameter of 25 inches, covered with a fabric layer on the inside.

Powdery carnauba wax was sieved over a sieve of 80 mesh in advance. The so prepared powdery carnauba wax was then sprinkled little by little over the tumbling soft capsules to accomplish coating. There were obtained capsules having carnauba wax coating films over the surfaces thereof. The water content of the shells of the so prepared soft capsules was 8%, and the amount of the carnauba wax coating film was 0.012%.

PREPARATION EXAMPLE 2

Three thounsand Oblong-3 type soft capsules, each of which contained 100 mg. of palmitate of Vitamin A and the total weight of the shells of which was 480 g. were charged and tumbled in a pan of inner diameter of 25 inches covered with a fabric layer.

Powdery carnauba wax was sieved over a sieve of 80 meshes in advance. The so prepared powdery carnauba wax was then sprinkled little by little over the tumbling soft capsule agents to accomplish coating. There were obtained capsules having carnauba wax coating films over the surfaces thereof. The water content of the shell of the so prepared soft capsule was 8%, and the amount of the carnauba wax coating film was 0.015%.

We claim:

1. A soft-gelatin capsule, comprising a core material containing a pharmaceutically active substance; a soft-gelatin shell encapsulating said core material, said soft-gelatin shell containing from about 5 to about 10% by weight of water; and a uniform coating film layer consisting of carnauba wax covering the external surface of said soft-gelatin shell, with the provisos that the amount of said carnauba wax is at least 0.002 parts by weight per 100 parts by weight of said shell when said shell contains about 5% by weight of water, the amount of said carnauba wax is at least 0.004 parts by weight per 100 parts by weight of said shell when said shell contains about 8% by weight of water, and the amount of said carnauba wax is at least 0.006 parts by weight per 100 parts by weight of said shell when said shell contains about 10% by weight of water.

2. A soft-gelatin capsule as claimed in claim 1, wherein the amount of said carnauba wax is not higher than 0.05 parts by weight per 100 parts by weight of said shell.

3. A coated soft capsule as claimed in claim 1, wherein the amount of said carnauba wax is not higher than 0.15 parts by weight per 100 parts by weight of said shell.

4. A process for coating soft-gelatin capsules comprising a core material containing a pharmaceutically active substance and a soft-gelatin shell encapsulating said core material, said shell containing from about 5 to about 10% by weight of water which consists essentially of: placing a quantity of said soft-gelatin capsules in a rotating coating pan so as to cause said capsules to tumble in said pan, sprinkling carnauba wax powder having a particle size of less than 80 mesh size onto said capsules and blowing warm air into said pan to melt said carnauba wax and cause it to form a uniform coating film of said capsules wherein the amount of carnauba wax coated on said capsules is at least 0.002 parts by weight per 100 parts by weight of said shell when said shell contains about 5% by weight of water, the amount of said carnauba wax coated on said capsules is at least 0.004 parts by weight per 100 parts by weight of said shell when said shell contains about 8% by weight of water, and the amount of said carnauba wax coated on said capsules is at least 0.006 parts by weight per 100 parts by weight of said shell when said shell contains about 10% by weight of water.

* * * * *